United States Patent
Doyle

(10) Patent No.: US 10,507,071 B2
(45) Date of Patent: Dec. 17, 2019

(54) HAND ACTUATED, ARTICULATING DEVICE HAVING AN ELECTRIC FORCE ENHANCEMENT SYSTEM

(75) Inventor: Mark Doyle, Del Mar, CA (US)

(73) Assignee: CAREFUSION 2200, INC., San Diego, CA (US)

( * ) Notice: Subject to any disclaimer, the term of this patent is extended or adjusted under 35 U.S.C. 154(b) by 1460 days.

(21) Appl. No.: 12/776,902

(22) Filed: May 10, 2010

(65) Prior Publication Data

US 2010/0286711 A1 Nov. 11, 2010

Related U.S. Application Data

(60) Provisional application No. 61/177,063, filed on May 11, 2009.

(51) Int. Cl.
*A61B 34/00* (2016.01)
*A61B 34/37* (2016.01)

(52) U.S. Cl.
CPC .............. *A61B 34/70* (2016.02); *A61B 34/37* (2016.02)

(58) Field of Classification Search
CPC ......... A61B 34/70; A61B 34/37; A61B 19/22; A61B 2019/2242
USPC ............................................... 606/1, 46, 130
See application file for complete search history.

(56) References Cited

U.S. PATENT DOCUMENTS

| | | | | |
|---|---|---|---|---|
| 5,235,225 A | * | 8/1993 | Colgate et al. | 310/309 |
| 5,431,645 A | * | 7/1995 | Smith | A61B 10/06 600/106 |
| 5,721,566 A | * | 2/1998 | Rosenberg et al. | 345/161 |
| 6,607,475 B2 | | 8/2003 | Doyle et al. | |
| 2002/0018046 A1 | * | 2/2002 | Rosenberg | 345/156 |
| 2003/0191454 A1 | * | 10/2003 | Niemeyer | 606/1 |
| 2007/0103437 A1 | * | 5/2007 | Rosenberg | G09B 23/285 345/161 |
| 2007/0142823 A1 | * | 6/2007 | Prisco et al. | 606/1 |
| 2008/0202274 A1 | * | 8/2008 | Stuart | B25J 9/106 74/490.02 |
| 2009/0054909 A1 | * | 2/2009 | Farritor et al. | 606/130 |
| 2010/0076475 A1 | * | 3/2010 | Yates et al. | 606/170 |

OTHER PUBLICATIONS

Definition of enhance. Merriam-Webster Dictionary, retrieved on Oct. 19, 2016; Retrieved from the Internet: <http://www.merriam-webster.com/dictionary/enhance>.*

* cited by examiner

*Primary Examiner* — Gary Jackson
*Assistant Examiner* — Sebastian X Lukjan
(74) *Attorney, Agent, or Firm* — Arent Fox LLP

(57) ABSTRACT

An articulating device element and methods of operation thereof, including a compensating force enhancement for compensating for any unwanted friction and/or other such resistance forces experienced by the device when being manipulated.

25 Claims, 5 Drawing Sheets

HAND ACTUATED, ARTICULATING DEVICE HAVING AN ELECTRIC FORCE ENHANCEMENT SYSTEM

CROSS-REFERENCE TO RELATED APPLICATION

This application claims the benefit of U.S. Provisional Application No. 61/177,063, filed on May 11, 2009, the contents of which is expressly incorporated by reference herein in its entirety.

BACKGROUND OF THE INVENTION

Field of the Invention

The present invention relates to hand-actuated articulating devices wherein the device includes an electric force enhancement system therein. One aspect of the present invention relates to a hand-actuated articulating surgical instrument for use in minimally invasive surgical procedures wherein the instrument includes an electric force enhancement system therein.

Background of the Related Art

Laparoscopic surgery is well known in the art. However, current laparoscopic surgical instruments typically have straight bodies that are rather awkward to use. While such existing laparoscopic surgical instruments can perform invasive surgical procedures, the instruments are awkward to manipulate around corners and other such hard to reach places. Moreover, existing laparoscopic surgical instruments typically use push rods, cables and hydraulic lines to manipulate the surgical tip of the instruments. As the size of existing laparoscopic surgical instruments is reduced, the hydraulic lines used therein are also being decreased in size as well. However, when the hydraulic lines decrease in size, manually forcing hydraulic fluid through the hydraulic lines becomes more difficult to accomplish. Moreover, if a surgeon is controlling the surgical instrument within the body from a distance or remote location from the patient, the hydraulic lines are relatively long, wherein manually forcing liquid through the hydraulic lines becomes difficult to accomplish. Furthermore, friction and unwanted resistive forces occur when moving the surgical instruments, thereby limiting the tactile feedback sensed by the surgeon.

Thus, during prolonged surgical procedures, or in cases where the surgeon is at a remote location relative to the instrument and patient, the surgeon typically experiences hand fatigue. Further, the friction produced while manipulating the surgical instrument masks or significantly limits the tactile feedback sensed by the surgeon.

Thus, there is a need in the art for a hand-actuated, articulating device that is easy to use, compensates for the friction or other resistance to motion, and reduces the hand fatigue experienced by the user. Further, there is a need in the art for a hand-actuated, articulating device that is capable of being easily manipulated around corners and other such hard to reach places.

SUMMARY OF THE INVENTION

While discussion of the aspects of the present invention that follows uses surgery for an illustrative purpose, it should be appreciated that the environment of the present invention is not limited to surgery and may be used in a variety of other environments. For example, aspects of the present invention may be used in manufacturing, construction, assembly lines, handling and disposing of hazardous materials, underwater manipulations, handling high temperature materials, or any other environment where a user may be remote from the item being manipulated or may experience fatigue when operating a mechanical device.

Aspects of the present invention aid a user, for example, a surgeon or other such medical practitioner in manipulating the hand-actuated articulating surgical instrument by providing an electric force enhancement thereto. The electric force enhancement compensates for the friction and unwanted resistive forces produced by the initiation of motion or a force input of the hand-actuated articulating surgical instrument within the patient. Additional aspects of the present invention provide a hand-actuated articulating surgical instrument that is capable of being manipulated around corners and functioning in hard to reach places.

In one aspect of the present invention, a surgeon inputs a force to the inventive surgical instrument, causing the surgical instrument to move in a direction of the inputted force. A sensing device detects that motion and/or a force of the inventive surgical instrument has been initiated and transmits a detected motion signal to an electric element. The electric element provides an electric force enhancement to the inventive surgical instrument, aiding the motion by compensating for any unwanted friction and/or other such resistance forces experienced by the instrument when being manipulated, e.g., by providing a compensating force acting in the same direction as the input, for example, within the patient.

In another aspect of the present invention, a control device may be used. When the sensing device detects that motion has been initiated, the sensing device sends a signal to the control device, which transmits a control signal to the electric element. The electric element emits a compensating force acting in the same direction as the input, to the inventive surgical instrument that is in the patient and aids the motion of the inventive surgical instrument by compensating for any unwanted friction and/or other such resistance forces experienced by the instrument when being manipulated within the patient.

Aspects of the present invention provide benefits and advantages that include the ability to compensate for friction and unwanted resistance that occurs when manipulating the surgical instrument within a patient. Thus, manipulating the surgical instrument within the patient is easier to accomplish and fatigue experienced by the surgeon is reduced. Further, compensating for the unwanted resistance of the instrument's motion increases the tactile feedback the surgeon feels when operating the surgical instrument. Additionally, the present invention creates a smooth force enhancement response to the motion inputted by the surgeon.

Aspects of the present invention aid the surgeon in manipulating the surgical instrument in the direction of the motion inputted by the surgeon. Moreover, the present invention is capable of achieving a high degree of articulation, thus being easier to manipulate around corners and function in hard to reach places.

Additional advantages and novel features relating to the present invention will be set forth in part in the description that follows, and in part will become more apparent to those skilled in the art upon examination of the following or upon learning by practice of aspects of the invention.

BRIEF DESCRIPTION OF THE DRAWINGS

The present invention will become fully understood from the detailed description given herein below and the accompanying drawings, which are given by way of illustration and example only and thus not limited with respect to aspects of the present invention, wherein.

DETAILED DESCRIPTION OF ASPECTS OF THE PRESENT INVENTION

Aspects of the present invention will now be described more fully hereinafter with reference to the accompanying drawings, in which variations and aspects of the present invention are shown. Aspects of the present invention may, however, be realized in many different forms and should not be construed as limited to the variations set forth herein; rather, the variations are provided so that this disclosure will be thorough and complete in the illustrative implementations, and will fully convey the scope thereof to those skilled in the art.

Unless otherwise defined, all technical and scientific terms used herein have the same meaning as commonly understood by one of ordinary skill in the art to which aspects of the present invention belong. The methods and examples provided herein are illustrative only and not intended to be limiting.

Figure 1:
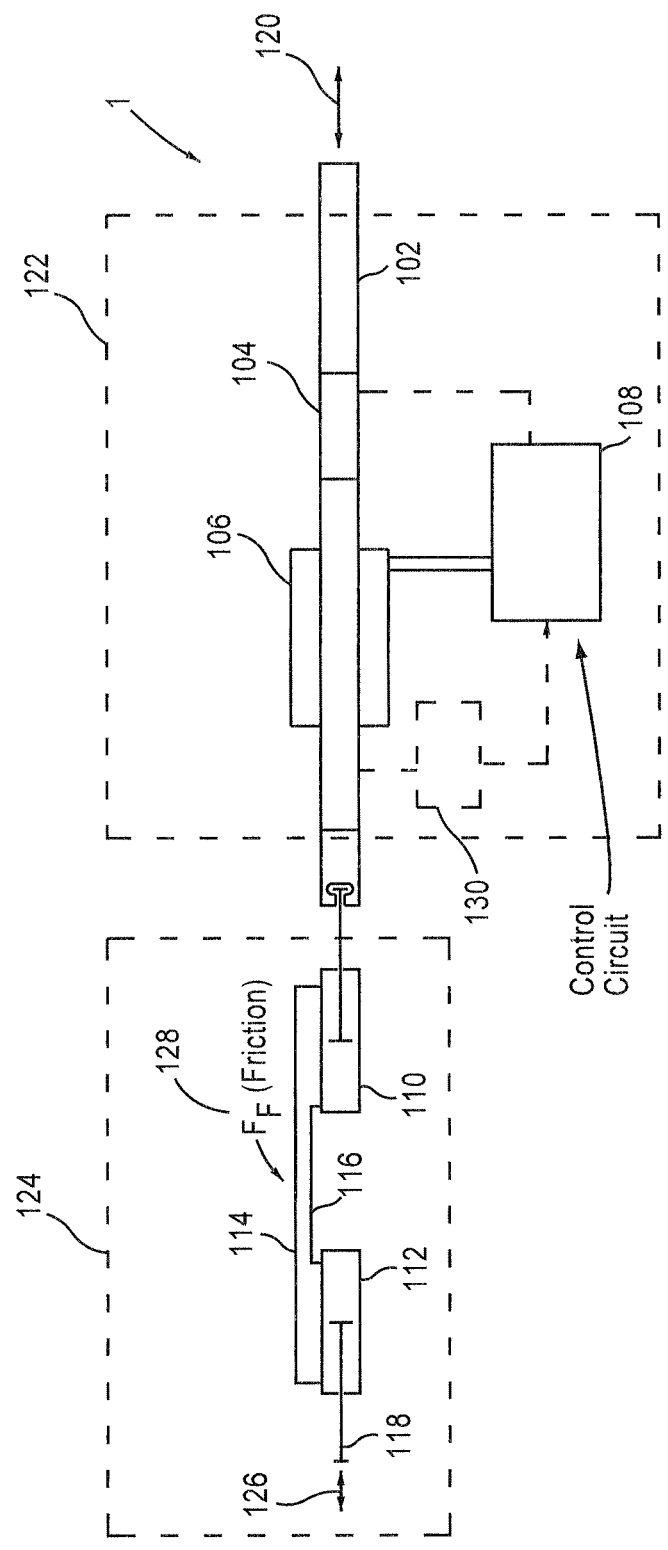
FIG. 1 is a schematic diagram of a hand-actuated, articulating surgical instrument having an electric force enhancement system in accordance with an aspect of the present invention.

Turning now to FIG. 1, illustrated is a hand actuated articulating device 1 in accordance with an aspect of the present invention. The device 1 includes an enhancement system 122 that receives one or more user inputs to direct a slave system 124 to perform work. The enhancement system 122 includes an input receiver 102, such as a shaft, that receives an input 120 from the user. The enhancement system 122 also includes an electric element 106 that assists in transferring the user input to the slave system 124 by providing an electric force enhancement that compensates for the friction and unwanted resistive forces produced by the initiation of motion and/or a force by the system. In an aspect, the electric force enhancement may be a compensating force acting in the same direction as the input assisting the motion of the system and compensating for the friction and unwanted resistive forces produced by the system. It should be appreciated that the work being performed by the system may result from mechanical transmissions through input receiver 102. The enhancement system 122 further includes a sensing element 104 that assists in activating the electric element 106 with an appropriate amount of power in the appropriate direction by detecting when a motion and/or force has been initiated by the user. In addition, the enhancement system 122 includes a control circuit 108 which assists in transferring the user input to the electric element 106.

Figure 2:
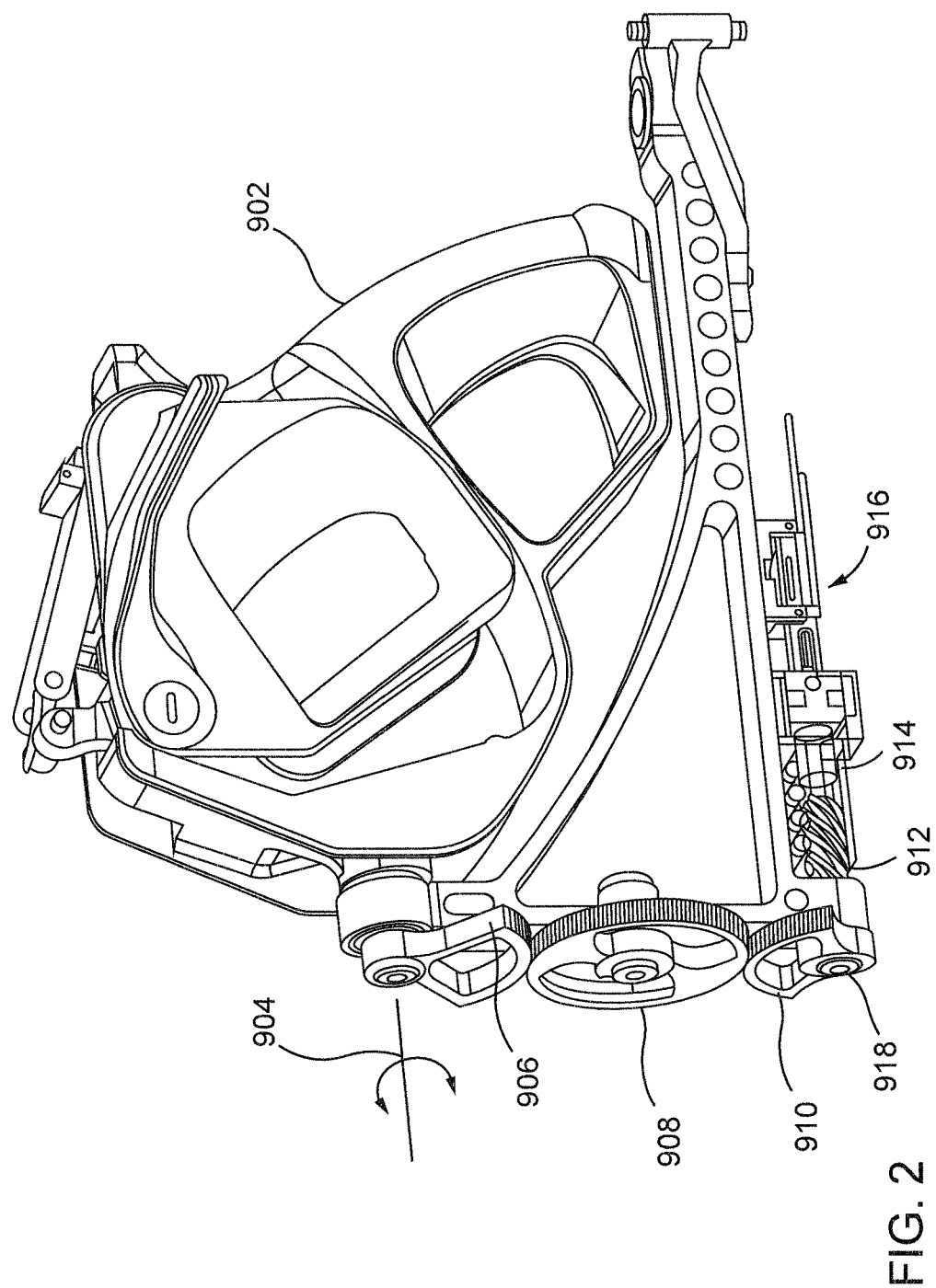
FIG. 2 is a side view of a control handle having rotary capability in accordance with an aspect of the present invention.

The shaft 102 may include, but is not limited to, any device or mechanism configured to receive one or more user inputs, and to transmit all or some portion of the user inputs, or a representation thereof, to the sensing element 104 and/or the electric element 106. As such, the shaft 102 is operationally connected to the electric element 106 with the sensing element 104 disposed between a proximal end of the shaft 102 and a proximal end of the electric element 106. For example, the shaft 102 may have one or more input mechanisms to receive hand- or finger-actuated inputs from a user of device 1. In other aspects, the shaft 102 may include input mechanisms to receive foot-actuated inputs, arm- or body-actuated inputs, etc. from the user. In further aspects, the shaft 102 may include input mechanisms to receive voice- or audio-actuate or eye-actuated inputs from the user. The input mechanisms may include, but is not limited to, one or more of for example, a joystick, a track ball, a rotary knob, an encoder, or a manipulator, among other input mechanisms. An example of an input mechanism is illustrated in FIG. 2.

The sensing element 104 detects the initiation of movement of the shaft 102 by the user. It should be appreciated that the sensing element 104, for example, may be, but is not limited to, being located on top of, below, covering, or surrounding the shaft 102. Additionally, the sensing element 104 may be directly or indirectly connected to the shaft 102. The sensing element 104 may be, but is not limited to for example, a strain gage, a small-displacement bipolar switch, a monopolar switch, two monopolar switches, a closing switch, an element which detects compression and tension, an element which detects torsion, an element which detects bending, an element which detects a resistant value changing in response to the force 120, an optical system which detects deflection or changes in the transmission of light in response to the force 120, or any other suitable sensing element that may detect motion initiation and/or force applied to the shaft 102. The sensing element 104 transmits a signal with the detected force and/or motion of the shaft 102 to the electric element 106.

The electric element 106 may be in series or parallel to the shaft 102 and the sensing element 104. Moreover, the electric element 106 may be directly or indirectly connected to the shaft 102. The electric element 106 may be, but is not limited to for example, a linear motor or a linear voice coil, a rotary motor, a rotary voice coil, or any other device that quickly responds to motion and may have a high frequency response. In addition, the control circuit 108 may be directly or indirectly connected to the sensing element 104 and the electric element 106. The control circuit 108 may receive a signal from the sensing device and transmits a control signal to the electric element 106. The control signal may include, but is not limited to for example, a current to energize the electric element 106 based upon the user input. It should be appreciated that the current may be variable, e.g., increase and/or decrease, based upon the user input. In addition, the control circuit 108 may be, but is not limited to, a series of non-programmable elements, one or more hard wired elements, a computer or a processor, among others. The control circuit 108 may also periodically perform a self-check prior to operation and/or a system check for determining whether the system is operating properly, e.g., determining whether the electric element 106 is providing the correct amount of force to compensate for the friction forces of the system. If the control circuit 108 determines that the electric element 106 is not providing the correct amount of force, then the control circuit 108 may modify the amount of current supplied to the electric element 106 to increase and/or reduce the amount of force provided by the electric element 106.

Optionally, in an aspect, the enhancement system 122 may also include an output sensor 130, e.g. a motion or a force sensor, operationally connected to the device and/or work piece and the control circuit 108. For example, if the output sensor 130 determines that the amount of force and/or movement of the electric element 106 is providing has dropped below the amount determined to compensate for the friction forces, then the output sensor 130 may send a signal to the control circuit to increase the current supplied to the electric element 106 to increase the compensating force. Alternatively, if the output sensor 130 determines that the amount of force and/or movement of being provided by the electric element 106 is above the amount determined to compensate for the friction forces, then the output sensor 130 may send a signal to the control circuit 108, which in turn decreases the current supplied to the electric element 106 to decrease the compensating force. Thus, the output sensor 130 may gauge the amount of force and/or movement being provided by the electric element 106 and assist in changing the current supplied to the electric element 106, e.g., ramping up and/or down the amount of current supplied to the electric element 106 to change the compensating force based on feedback based on actual output.

In addition, it should be appreciated that other sensors may be employed in helping to control the current supplied to the electric element 106. The sensors may include, but are not limited to for example, velocity, acceleration, deflection, temperature, angle, pressure, mass, weight, or position sensors, among others. In one aspect, acceleration sensors may be used by the control circuit 108 to learn the characteristics of the surgeon's hand motions in order to adjust the ramp up and/or ramp down of electric power provided to the electric element 106. In another aspect, angle sensors may be used by the control circuit 108 to determine the angular position or attitude of the device and in response to adjust the current.

Further, the slave system 124 is operationally connected to a distal end of the shaft 102. The slave system 124 may be any device or mechanism configured to receive one or more inputs, such as user inputs or representations thereof, from the shaft 102, and generate a corresponding output to control the functioning end 118 in a manner proportional to, or as a function of, the original user input 120. For example, in an aspect, the slave system 124 includes, but is not limited to, a double-acting closed loop hydraulic system including a control cylinder 110 operationally connected to a slave cylinder 112 by hydraulic control lines 114 and 116. Additionally, a functioning end 118 is operationally connected to a distal end of the slave cylinder 112. In this aspect, the closed loop double-acting hydraulic circuit is the basic mechanical element used to transmit force to the distal end of the device 1, e.g., the slave system 124. For example, the control cylinder 110 receives an input, such as all or a portion of a user input or representation thereof, and transmits the input via the hydraulic control lines 114 or 116 to slave cylinder 112, which generates an output used to drive the functioning end 118 of the slave system 124. In these aspects, the closed loop double-acting hydraulic system has the same or similar functionality as disclosed in U.S. Pat. No. 6,607,475 which is incorporated herein in its entirety by reference. In another aspect, the slave system 124 and the enhancement system 122 may be integrated into a single system. In an alternative aspect, the slave cylinder 112 and control cylinder 110 may be replaced with a mechanical element operationally connected to a distal end of the shaft 102 and a proximal end of the functioning end 118. The mechanical element may be, but is not limited to for example, linkage gears, cams, a series of u-joints, push-pull wire or cable, a cable/pulley system, a cable gear shift system, a push-pull chain, a push-pull-rotate chain, lead screws, a push-pull flexible strap, a flexible steel band, or any combination of these mechanical elements (e.g. a series of u-joints and a push-pull chain), among other mechanical elements which may cause fatigue when a user manipulates the mechanical elements.

The functioning end 118 receives as an input the output from the corresponding slave system 124, and in response performs some work that is controlled as a function of one or more of the original user inputs 120 received by the shaft 102. As such, the functioning end 118 may include or may be connected to any one or combination of devices or mechanisms configured to perform any type of work. In an aspect of the present invention, the functioning end 118 may include or may be connected to a variety of tools. For example, but not limited hereto, the functioning end 118 may include or may be connected to a surgical tool, surgical instrument, scissors, knives, screwdrivers, clamps, or pliers, among other tools.

In addition, the shaft 102 may have, but is not limited to, a structure such as solid, hollow or a "C" shape. In an aspect where the shaft 102 is solid, the hydraulic lines and the electric circuitry may be connected to the outside of the shaft 102. In an aspect where the shaft 102 is hollow, the hydraulic lines and the electric circuitry may be inside the shaft 102, passing through a lumen. Further, in aspect where the shaft 102 is a "C" shape, there may be a longitudinal slit or other shaped aperture in the shaft allowing the hydraulic lines and electric circuitry to pass both inside and outside the shaft 102.

In one variation, the enhancement system 122 is located outside of the patient's body, e.g., connected to and supported by the operating room table. In other aspects, the enhancement system 122 may be located remote from the slave system 124, e.g., in another room or location. Appropriate wired and/or wireless connections can be made between the enhancement system 122 and the slave system 124.

In operation, the user's hands, arms and/or fingers, for example, may guide the movement of device 1 by applying a force 120 to the proximal end of the shaft 102. The force 120 is transmitted to the shaft 102, moving the shaft 102 in a direction corresponding to a direction of the force 120. For example, if the user inputs a linear pushing force, then a compensating force aids the movement of the mechanical load (e.g. the shaft in a linear direction). The force compensates for one or more friction forces produced by moving the shaft 102 in the direction of the force 120. For example, the friction forces may include friction forces 128 caused by resistance in moving fluid through hydraulic control lines 114 and 116.

In an aspect, an equation for determining the set point for the compensating force may include:

$$F_c = C \cdot F_p, \text{ where} \quad (1)$$

$C \leq 1$, and $F_c$ is the electric compensation force, e.g., the force provided by the electric element 106; $F_p$ is the parasitic system force, e.g., the friction and/or unwanted resistive forces produced by moving the system; and C is the compensating force typically set below the parasitic system force $F_p$. For example, if $C=0.9$, then the electric compensation force provided would be 90% of the parasitic system force, e.g., $F_c = (0.9)(F_p)$.

In addition, if the compensation force, as discussed above in regards to equation (1), is not applied to the force inputted by the user, then the force inputted by the user may be calculated using the following equation:

$$F_i = F_p + F_r, \quad (2)$$

where $F_i$ is the force inputted by the user, e.g., force 120; $F_p$ is the parasitic system force; and $F_r$ is the reaction force by target. Thus, when the compensating force is not applied to the user's input, the user senses both the reaction forces by the target and the friction forces of the system when applying force to the device.

However, if the force inputted by the user does include the compensating force, as discussed above in regards to equation (1), then the force inputted by the user may be calculated using the following equation:

$$F_i = F_p - F_c + F_r, \quad (3)$$

where $F_i$ is the force inputted by the user, e.g., force 120; $F_p$ is the parasitic system force; $F_c$ is the electric compensation force, as calculated above in regards to equation (1); and $F_r$ is the reaction force by target. Thus, when the compensating force is applied to the user's input, the user senses the resistance for the work being performed and not the friction forces of the system, e.g., moving hydraulic fluid through the system.

The compensating force may be a preset factor (e.g., at the factory or in the operating room, among other locations) or the compensating force may be a self-learned factor from measuring the resistance to moving the shaft. In an aspect, the preset factor may be set above or below the friction forces 128 associated with moving the shaft 102 or some fraction thereof. It should be appreciated that the motion of the shaft 102 may be, for example, pushing, pulling, rotating, moving to the left, moving to the right, moving upwards, moving downwards, bending, spinning, moving diagonally, or any other direction that may be necessary for device 1 to move. Further, in an alternative, the user may apply force 120 to an input mechanism, not shown, that is operationally connected to the shaft 102.

Figure 3:
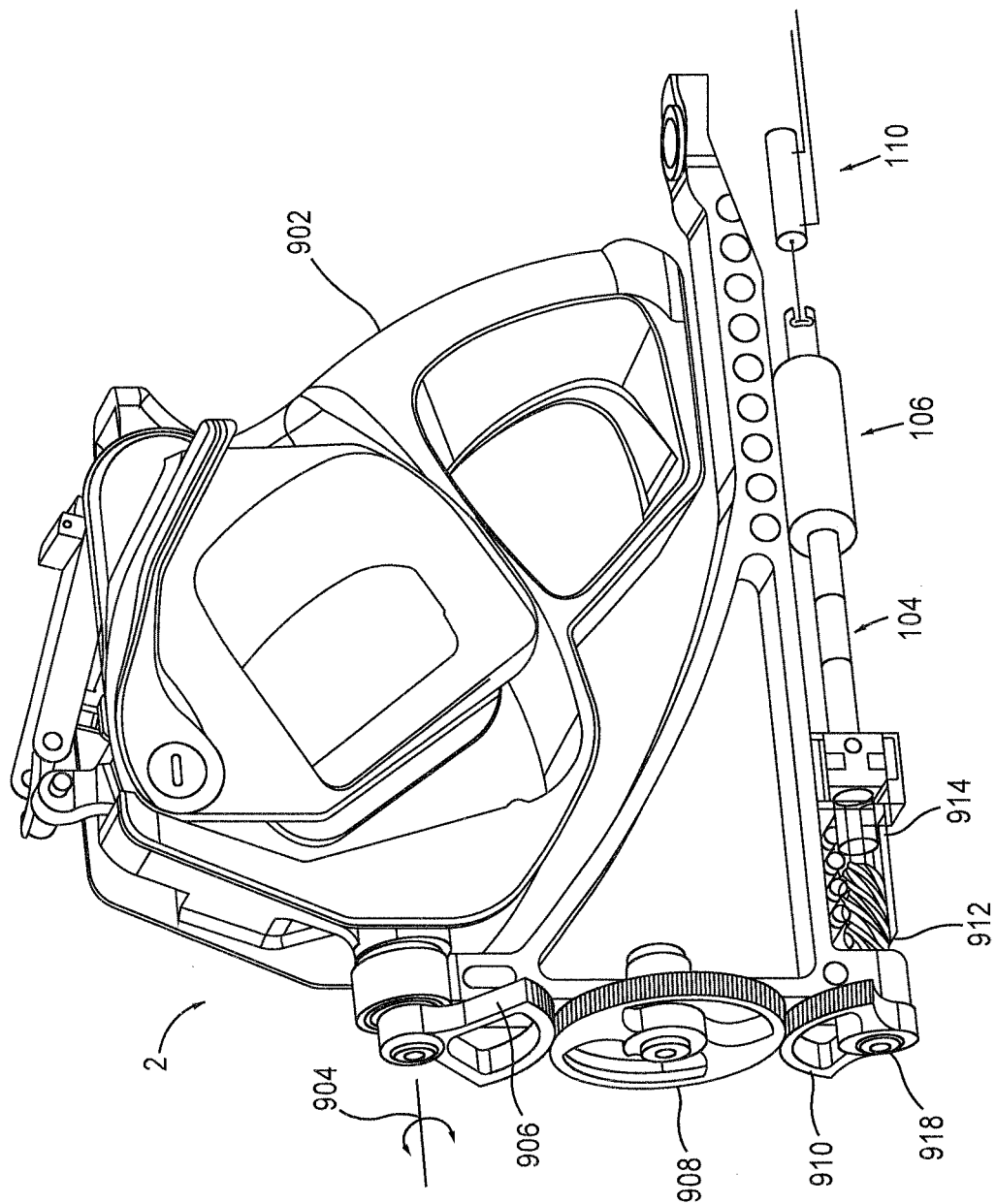
FIG. 3 is a side view of a control handle having rotary capability coupled to an electric force enhancement system in accordance with an aspect of the present invention.

Referring now to FIG. 2, illustrated is an example of a control handle input mechanism 902 that may receive inputs from a user and transfer the inputs to device 1 (FIG. 1). The control handle 902 rotates around a first axis 904 and is operationally connected to a first pendulum gear 906. The motion and/or force initiated from rotating the control handle 902 around the first axis 904 causes the first pendulum gear 906 to rotate, for example, in a swinging motion around the first axis 904. The swinging motion of the first pendulum gear 906 rotates an intermediate gear 908. The intermediate gear 908 is disposed between the first pendulum gear 906 and a second pendulum gear 910. The rotation from the intermediate gear 908 causes the second pendulum gear 910 to rotate in a swinging motion around a second axis 918 to which the second pendulum gear 910 is operationally connected to the second axis 918, wherein the second axis 918 is defined by a lead screw 912. The swinging motion of the second pendulum gear 910 causes the lead screw 912 to rotate around the second axis 918. A lead nut 914 is disposed between and operationally connected to the lead screw 912 and a hydraulic cylinder 916. The motion and/or force initiated from rotating the lead screw 912 causes the shaft of the hydraulic cylinder 916 to move along the second axis. In an aspect, the hydraulic cylinder 916 may be operationally connected to the lead nut 914 wherein the movement of the lead screw 912 creates the force 120 input to the lead nut 914. It should be understood that input mechanism 902 is only one, non-limiting example of an input mechanism operable with device 1. It should also be understood that the lead nut 914 may be operationally connected to the enhancement system 122 (FIG. 1), as illustrated in FIG. 3.

Turning back to FIG. 1, the sensing element 104 detects the initiation of movement of the shaft 102. The sensing element 104 may be, but is not limited to for example, a strain gage, a small-displacement bipolar switch, monopolar switches, a closing switch, an element which detects compression and tension, an element which detects a resistant value changing in response to the force 120, an optical system which detects deflection or changes in the transmission of light in response to the force 120, or any other suitable sensing element that may detect motion initiation and/or force applied to the shaft 102. The sensing element 104 transmits a signal with the detected force and/or motion of the shaft 102 to the control circuit 108, activating the electric element 106 in an appropriate direction. In addition, in one aspect, the output from the sensing element 104 may be transmitted to the control circuit 108 for appropriately varying the current to the electric element 106. For example, the control circuit 108 may determine how quickly the electric element 106 should move based upon the detected force and/or motion from the sensing element 104, e.g., ramps up and/or down the movement of the electric element 106 based upon the user input 120. Thus, the amount of force provided by the electric element 106 may be variable based upon the force and/or speed of the user input. It should be appreciated that the electric element 106 may be, but is not limited to among others, a voice coil, a linear motor, or any other device that quickly responds to the initiation of motion and/or a force input and may have a high frequency response.

The electric element 106 responds to the signal transmitted from the sensing element 104 by emitting a force to the shaft 102 in the same direction as the force 120. The force aids the user in moving the shaft 102 in the direction of the force 120. For example, if the user wants to move the shaft 102 to the left, the sensing element 104 detects the initiation of motion and/or a force input to the shaft 102 and activates the electric element 106 to emit a force aiding the user in moving the shaft 102 to the left. The force compensates for the friction forces 128 produced by moving the shaft 102 allowing the user to sense the reaction forces 126 and not the friction forces 128. In an aspect of the present invention, the sensing element 104 transmits a signal with the detected motion of the shaft 102 to the control circuit 108.

The control circuit 108 may be, but is not limited to, a series of non-programmable elements, one or more hard wired elements, a computer, or a processor, among other control circuits. The control circuit 108 transmits a signal, e.g., a power signal, to the electric element 106 causing the electric element to emit a force in the same direction as force 120. The force compensates for the friction forces 128 produced by moving the shaft 102 allowing the user to sense the reaction forces 126, not the friction forces, such as friction force 128. It should be appreciated that the force produced by electric element 106 is approximately equal to the resistance to motion, for example friction, of the shaft 102 in the direction of force 120. Resistance forces, which may be variable based upon, for example, but not limited to, temperature of the patient, position of the device 1, the device 1 entering and existing surgical ports, the lubrication of the hydraulic lines, position of the hydraulic lines, e.g., straight or coiled around a bend, the axis of movement, the type of surgical procedure being performed, temperature of the operating room, time, and any other factor which may cause the friction force 128 to change.

Further, it should be appreciated that the force emitted by electric element 106 may be a preset factor near the resistance to motion of the device 1. In an aspect, the preset factor may be set above or below the friction forces 128 of the shaft 102 or some fraction thereof. For example, if the friction force 128 for moving the mechanical load (e.g. moving the shaft 102 in a direction corresponding to a direction of the force 120) is equal to 1 pound (lb), then the preset factor may be set at 0.9 resulting in a compensation force of 0.9 lb. It should be appreciated if the preset factor is set above the force of friction, the user may need to control and/or restrain the system to prevent unexpected movements from the shaft 102. For example, the value of the preset factor may be set by a manufacturer, by a user adjusting the value of the preset factor to a user's specific comfort level, or the value of the preset factor may be self-learned. It should be appreciated that when the user is adjusting the value of the preset factor, they may have a potentiometer, or a control panel, for example, on the input device the user is using. Thus, if the user has control handles operationally connected to the shaft 102, the control panel/handles may have a potentiometer which the user uses to adjust the value of the preset factor for the force produced by the electric element 106, for example. In accordance with an aspect of the present invention, once the value of the force produced by the electric element 106 is set, the value of the force may not change substantially.

It should be appreciated that when the preset factor may be self-learned, for example during a startup procedure in which the system self-determines the preset factors, the current supplied to the electric element 106 may be increased until the shaft 102 moves an incremental distance as detected by sensor 130 and control circuit 108 may thereby learn how much current is needed to make the shaft 102 move. Further, control circuit 108 may be a processor, for example, for setting the preset factor below the current level learned when the electric element 106 moves the shaft 102. Once the preset factor has been set, the control circuit 108 instructs the electric element 106 to produce a force, at the preset factor, on the shaft 102 in the same direction as force 120.

In accordance with another aspect of the present invention, the force produced by electric element 106 may be a servo function which increases the force produced by the electric element 106 in response to the force 120 by the user. Thus, the value of the force the electric element 106 produces varies in response to the force 120.

The shaft 102 controls the movement of the mechanical device 1 corresponding to the direction of the force 120 by transmitting the force 120 to control cylinder 110. For example, if the user pushes, pulls, rotates, moves to the left, moves to the right, moves upwards, moves downwards, bends their wrist or fingers, or spins the input device operationally connected to the shaft 102, the control cylinder 110 moves in the same direction. It should be appreciated that the control cylinder 110, slave cylinder 112, hydraulic control tubes 114 and 116, and a functioning end 118 may be included in the closed loop double-acting hydraulic circuit 124. The closed loop double-acting hydraulic circuit 124 is the basic mechanical element used to transmit force to the distal end of the surgical instrument which is in the patient. Further, in an aspect, the closed loop double-acting hydraulic circuit 124 may have substantially the same functionality as disclosed in U.S. Pat. No. 6,607,475 which is incorporated herein in its entirety by reference.

Control cylinder 110 transmits the force 120 to the slave cylinder 112 by moving fluid through hydraulic control lines 114 and 116. It should be appreciated that the fluid may be any suitable hydraulic fluid, known or later developed, but preferably is either water or saline. A functioning end 118 is operationally connected to the distal end of slave cylinder 112. The slave cylinder 112 actuates the movement of the functioning end 118 in the direction of the force 120. It should be appreciated that the functioning end 118 may be a surgical tool, surgical instruments, or any other device that may be used in surgery. In an aspect, the functioning end 118 may be or may be connected to a variety of tools. For example, the tools may be wrenches, scissors, screwdrivers, clamps, knives, pliers, or cutters, among other tools.

Referring now to FIG. 3, illustrated is a device 2 where control handle 902 (FIG. 2) is operationally coupled to an example enhancement system 122 (FIG. 1) in accordance with an aspect of the present invention. It should be understood that the control handle 902 and the enhancement system 122 have similar functionality and reference numbers as the control handle described with regards to FIG. 2 and the enhancement system 122 as described with regards to FIG. 1.

In this aspect, the lead nut 914 is disposed between and operationally connected to the lead screw 912 and the sensing element 104 (FIG. 1). Thus, the motion and/or force initiated from rotating the control handle 902 around the first axis 904 causes the movement of the lead screw 912 and transfers a function of the input force 120 to the lead nut 914. The sensing element 104 detects the initiation of movement of the lead nut 914 and transmits a signal with the detected motion and/or force of the lead nut 914 to the electric element 106 operationally connected to the sensing element 104, activating the electric element 106 in an appropriate direction. The electric element 106 responds to the signal transmitted from the sensing element 104 by emitting a force to the hydraulic cylinder 110 in the same direction as the force 120 (FIG. 1). Thus, the compensating force provided by the electric element 106 aids the user in moving the device 2 in the direction of the input force 120.

Figure 4:
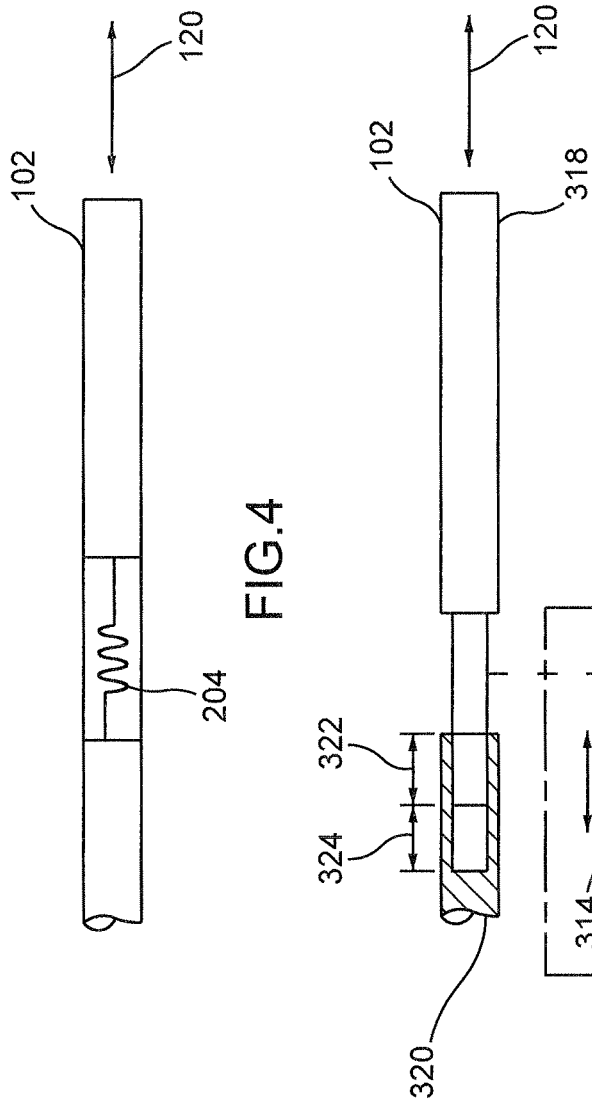
FIG. 4 is a schematic diagram of a strain gage type sensing element used with the present invention.

Referring to FIG. 4, in accordance with an aspect of the present invention, sensing device 104 (FIG. 1) may be a strain gage sensor 204. For example, strain gage sensor 204 may be operationally connected to the distal end of the shaft 102. Strain gage sensor 204 detects the force 120 on the shaft 102, e.g., the compression and tension on the shaft 102. For example, if the user pushes the shaft 102, then strain gage sensor 204 detects that the shaft 102 compresses. Thus, the strain gage sensor 204 provides variable output based upon the amount of force provided by the user and the rate of the input, e.g., the speed at which the user is applying the force.

It should be appreciated that strain gage sensor 204 detects other directions the user may move the shaft 102. For example, the user may move the shaft 102 by pulling, rotating, moving to the left, moving to the right, moving upwards, moving downwards, bending, spinning, moving diagonally, or any other direction that may be necessary for the device 1 to move. Further, it should be appreciated that the control circuit, as discussed above in reference to FIG. 1, may be used in this aspect of the present invention, but is not necessary.

Figure 5:
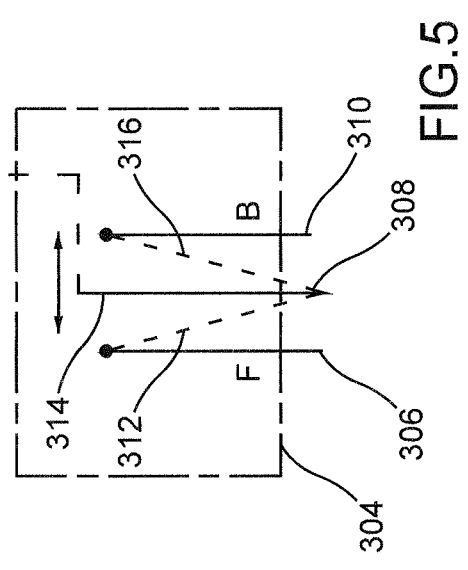
FIG. 5 is a schematic diagram of a switch type sensing element used with the present invention.

Referring to FIG. 5, in accordance with another aspect of the present invention, sensing device 104 may include a switch sensing element 304. It should be appreciated that switch 304 may be a low travel bi-pole switch, for example. The switch sensing element 304 is operationally connected to the shaft 102 between a proximal end of the shaft 102 and a proximal end of the electric element 106. In another aspect, the switch sensing element 304 may be operationally connected above, below or surrounding the shaft 102. The switch sensing element 304 detects the force 120 on the shaft 102 by connecting either one pole or another pole. Thus, the switch sensing element 304 sends a current to electric element 106 depending on which pole is connected, activating the electric element 106. In an appropriate direction. Further, there may be a potentiometer, or similar device, to set the value of the compensating force produced by electric element 106. It should be appreciated that in this aspect of the present invention a control circuit, as discussed above in reference to FIG. 1, may be used, but is not necessary.

Referring to FIG. 5, optionally, the described aspects may further include shaft 102 having an amount of compliance between an input end 318 and an output end 320 to compensate for the force required to initiate movement of the system. In other words, to avoid a user feeling the unwanted friction and/or other resistance forces 128 (FIG. 1) in system 1 (FIG. 1) when initially providing input 120, this optional aspect allows input end 318 of shaft 102 to move relative to output end 320 until enhancement system 122 (FIG. 1) can be energized to overcome the unwanted friction and/or other resistance forces 128 (FIG. 1). This avoids the user applying additional input to overcome the unwanted friction and/or other resistance forces of the system and having the unwanted friction and/or other resistance forces abruptly removed when the enhancement system 122 (FIG. 1) activates.

As illustrated in FIG. 5, the center pole 308 of sensing element 304 may move forward towards the direction of pole 306 and backwards towards the direction of pole 310, e.g., between a neutral position 314, a forward position 312, and a backward position 316. In an aspect, the distance the shaft 102 moves to change the center pole 308 between the neutral position 314 and either the forward or backward position 312 or 316, respectively, corresponds to the forward or backward compliance 324 or 322, respectively, in the shaft 102. For example, if the user input 120 is in a forward direction, when shaft 102 makes initial contact with sensing element 304, center pole 308 may travel a short distance forward before making contact with pole 306 at forward position 312. The described aspects may provide an amount of compliance in shaft 102 to compensate for the amount of force necessary to move the shaft 102 in the direction of pole 306 while allowing the system time to energize. For example, the described aspects may permit the sensing element 304 to initiate the electric element 106 (FIG. 1) before, or as, motion of the slave system 124 (FIG. 1) begins so the user does not feel the force required to move the system, and thus, providing device 1 time to energize and help the user compensate for the friction and unwanted resistive forces produced by the initiation of motion and/or forces by the system. It should be appreciated that this is one non-limiting example of providing for compliance in the system and that various aspects of the present invention may need to compensate for compliance.

Figure 6:
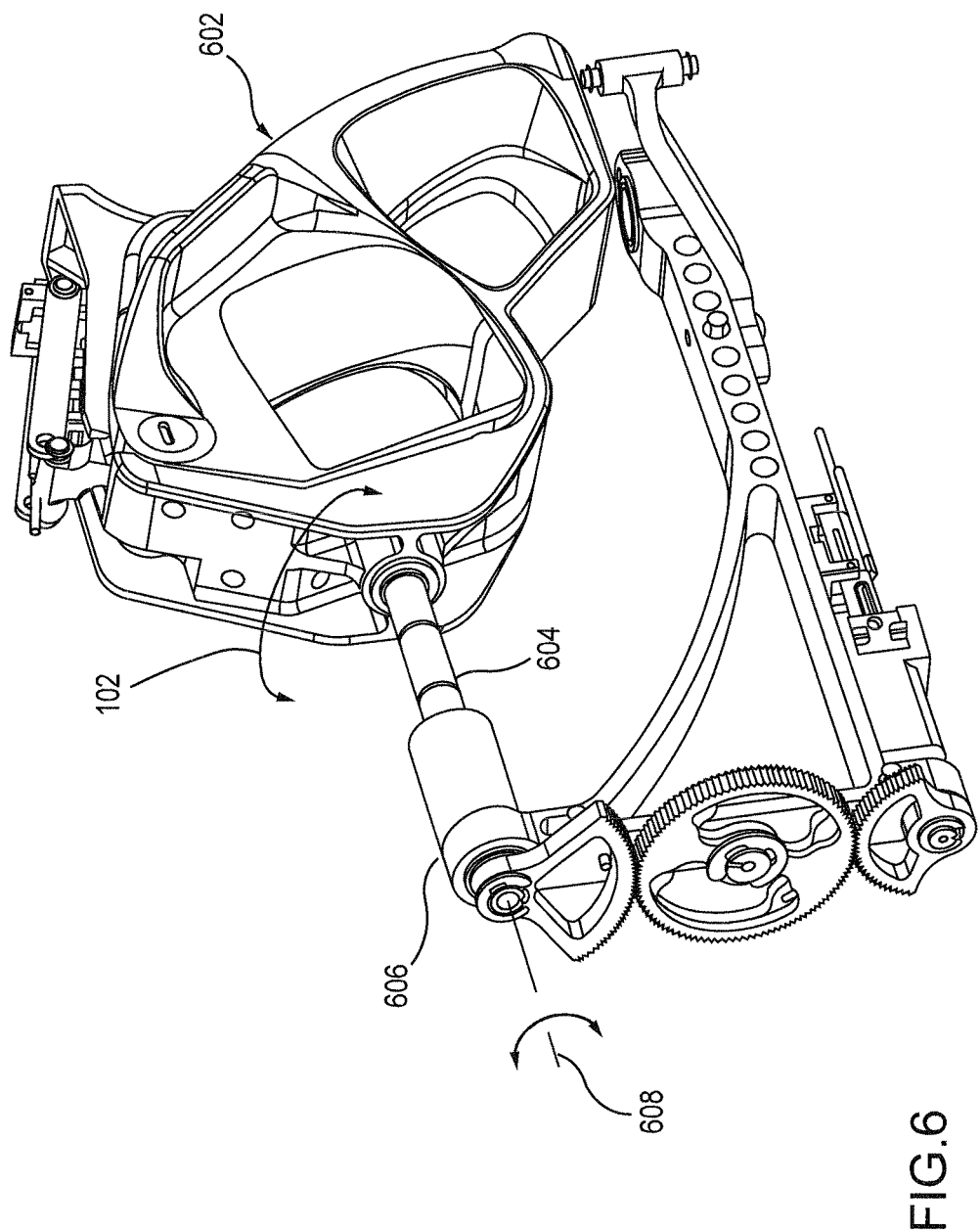
FIG. 6 is a side view of a rotary sensing element and a rotary electric element in accordance with an aspect of the present invention.

Referring to FIG. 6, in accordance with an aspect of the present invention, sensing device 104 may be a torsion sensing element 604 and electric element 106 may be a rotary electric element 606. Torsion sensing element 604 may be operationally connected to the input mechanism 602 and the rotary electric element 606. In one non-limiting example, the rotary electric element 606 may be concentric to axis 608 and in series with the torsion sensing element 604. For example, in operation of an aspect, the user's hands, arms and/or fingers, for example, may guide the movement of the input mechanism 602 by applying a force 120, e.g., rotating and/or turning, to the input mechanism 602. Torsion sensing element 604 detects the force 120 on the input mechanism 602 and activates the rotary electric element 606 in the appropriate direction and/or amount. For example, if the user rotates or turns the input mechanism 602, then the torsion sensing element 604 detects the direction of the rotation, activating the rotary electric element 606 in an appropriate direction of the force 120. It should be appreciated that in this aspect of the present invention, a control circuit, as discussed above in reference to FIG. 1, may be used, but is not necessary.

One variation of the present invention may include a user controlling multiple sensing elements and electric elements for creating different motions. For example, there may be individual systems for pushing, pulling, rotating, moving to the left, moving to the right, moving upwards, moving downwards, bending, spinning, moving diagonally, among other systems. The individual systems activate by reacting to the appropriate user hand motion. Further, each individual system may compensate for different friction characteristics according to the motion performed by the particular system.

Another variation of the present invention may include using mechanical vacuum pressure and/or pressure assist instead of an electric element, as described above. For example, the user manipulates a dual acting diaphragm and a valve. Thus, as the user moves the surgical instrument forward, a valve admits vacuum to one side of the diaphragm helping the user move forward. In addition, if the user pulls backs the surgical instrument, the valve reverses and helps the user pull the surgical instrument back.

Although the invention has been described with reference to various aspects of the present invention and examples with respect to a surgical instrument, it is within the scope and spirit of the invention to incorporate or use with any suitable mechanical device. Further, while the invention has been described with reference to a surgeon, the invention may be used with another user, depending on circumstances in which the invention is used. Thus, it should be understood that numerous and various modifications may be made without departing from the spirit of the invention.

What is claimed is:

1. An articulating device, comprising:
   a hydraulically-driven system comprising:
   a hydraulic input receiver capable of receiving an input as an external force in at least a first direction;
   a hydraulically driven slave system coupled to the hydraulic input receiver operable to receive the external force in the at least the first direction from the hydraulic input receiver and generate a corresponding hydraulic output, wherein the hydraulically driven slave system comprises a first hydraulically driven slave end coupled to the hydraulic input receiver and a second hydraulically driven slave end;
   a hydraulically driven functioning end coupled to the second hydraulically driven slave end, wherein the hydraulically driven functioning end performs the output; and
   an electrically-driven enhancement system connected with the hydraulically-driven system and configured to provide an electric force enhancement during operation of the hydraulically-driven system by providing a compensating force in the at least the first direction to the hydraulically driven slave system, wherein the electrically-driven enhancement system comprises:
   a sensing element coupled to the hydraulic input receiver and operable to detect the received input from the external force on the hydraulic input receiver;

a force enhancement electric element operatively connected to the sensing element and the hydraulic input receiver configured to transfer a function of the detected input from the sensing element to the slave system; and
a control circuit element which is coupled to the sensing element and the force enhancement electric element, wherein the control circuit element is configured to transmit a control signal to the force enhancement electric element based on a detected input from the sensing element, wherein the enhancement electric element outputs a compensating force based on the control signal, wherein the compensating force compensates for resistance forces in moving the hydraulic input receiver by enhancing the external force received at the hydraulic input receiver.

2. The articulating device of claim 1, wherein the control circuit is further operable to calculate the resistance forces produced by the articulating device and supply the control signal to the element to emit the compensating force based upon the calculated resistance forces.

3. The articulating device of claim 1, wherein the control signal transmitted to the element includes a current to energize the element, wherein the current is variable based upon the force of the input.

4. The articulating device of claim 1, wherein the control circuit is further operable to diagnose whether the articulating device is operating correctly.

5. The articulating device of claim 1, wherein the compensating force is a percentage of resistance forces produced by the articulating device.

6. The articulating device of claim 1, wherein the compensating force is set by a user.

7. The articulating device of claim 1, wherein the compensating force is self-learned by measuring resistance when moving the input receiver.

8. The articulating device of claim 1, wherein the compensating force is variable based upon the speed and force of the input.

9. The articulating device of claim 1, wherein the slave system comprises a closed loop double-acting hydraulic system.

10. The articulating device of claim 1, wherein the slave system further comprises a mechanical element.

11. The articulating device of claim 10, wherein the mechanical element comprises at least one of linkages, gears, cams, a series of u-joints, a push-pull chain, lead screws, cable-pulley system, or a flexible steel band.

12. The articulating device of claim 1, wherein the functioning end comprises one of a surgical tool, a surgical instrument, scissors, a knife, a screwdriver, a clamp, or pliers.

13. The articulating device of claim 1, wherein the sensing element is one of strain gage, a bipolar switch, a closing switch, or an optical system.

14. The articulating device of claim 1, wherein the element is one of a voice coil, or a linear motor.

15. The articulating device of claim 1, wherein the force enhancement electric element is coupled in series to the input receiver and the sensing element.

16. The articulating device of claim 1, wherein the force electric element is coupled in parallel to the input receiver and the sensing element.

17. A device comprising:
a hydraulically-driven mechanical system capable of receiving an input, as an external force in at least a first direction;
a sensor coupled to the hydraulically-driven mechanical system operable to detect the received input;
an electrically-driven enhancement system connected with the hydraulically-driven mechanical system and providing an electric force enhancement during operation of the hydraulically-driven mechanical system by providing a compensating force to a hydraulically driven slave system of the hydraulically-driven mechanical system the compensating force acting on the hydraulically-driven mechanical system in the at least the first direction, wherein the electrically-driven enhancement system comprises:
a force enhancement electric element coupled to the hydraulically-driven mechanical system configured to transfer a function of the detected input from the external force and the compensating force, wherein the compensating force enhances the external force; and
a control circuit element which is coupled to the sensor and the force cement electric element and configured to transmit a control signal to energize the force enhancement electric element in the direction of the received input, wherein the enhancement electric element outputs a compensating force based on the control signal, wherein the compensating force compensating for resistance force in moving the hydraulic input receiver by enhancing the external force received at the hydraulic input receiver.

18. The device of claim 17, wherein the sensor is in series with the mechanical system.

19. The device of claim 17, wherein the sensor is in, parallel with the mechanical system.

20. The device of claim 17, wherein the force enhancement electric element is in series with the mechanical system.

21. The device of claim 17, wherein the force enhancement electric element is in parallel with the mechanical system.

22. A method comprising;
detecting, via a sensor, an external input force applied to a hydraulic input receiver in at least a first direction;
providing an electrically-driven compensating force to the external input force by an electrically-driven enhancement system, wherein the electronically driven enhancement system outputs a compensating force based on a control signal provided by a control circuit when the external input force is detected via the sensor, wherein the compensating force compensates for resistance forces in moving the hydraulic input receiver by enhancing the external force received at the hydraulic input receiver;
transmitting a function of the detected external input force, including the compensating force, from the electrically-driven enhancement system to a hydraulically-driven slave system coupled to the input receiver and connected with the electrically-driven enhancement system, wherein the compensating force enhances the function of the detected external input force during operation of the hydraulically-driven mechanical system; and
generating, at the slave system, a corresponding output to the detected external input force.

23. The articulating device of claim 1, wherein the compensating force aids the motion of the input receiver.

24. The device of claim 17, wherein the control circuit element is further operable to determine whether the force enhancement electric element is providing a correct amount of the compensating force.

25. The device of claim 24, wherein the control circuit element is operable to modify the control signal based on the determination.

* * * * *